(12) United States Patent
De Gasparo et al.

(10) Patent No.: US 6,174,910 B1
(45) Date of Patent: Jan. 16, 2001

(54) AT$_1$ RECEPTOR ANTAGONIST FOR THE STIMULATION OF APOPTOSIS

(75) Inventors: Marc De Gasparo, Rossemaison; Gillian Rosemary Bullock, Basel; Leoluca Criscione, Möhlin, all of (CH)

(73) Assignee: Novartis AG, Basel (CH)

( * ) Notice: Under 35 U.S.C. 154(b), the term of this patent shall be extended for 0 days.

(21) Appl. No.: 09/142,003

(22) PCT Filed: Feb. 18, 1997

(86) PCT No.: PCT/EP97/00757

§ 371 Date: Aug. 28, 1998

§ 102(e) Date: Aug. 28, 1998

(87) PCT Pub. No.: WO97/31634

PCT Pub. Date: Sep. 4, 1997

(30) Foreign Application Priority Data

Feb. 29, 1996 (CH) .................................................. 522/96

(51) Int. Cl.$^7$ ........................................... A61K 31/41
(52) U.S. Cl. ................. 514/381; 514/299; 514/300; 514/311; 514/314; 514/337; 514/338; 514/339; 514/340; 514/341; 514/342; 514/382; 514/386; 514/387; 514/390; 514/392; 514/393; 514/394; 514/395; 514/396; 514/397; 514/398; 514/399; 514/400
(58) Field of Search ................... 514/381, 382, 514/386, 387, 390, 392, 393, 394, 395, 396, 397, 398, 399, 400, 299, 300, 311, 314, 337, 338, 339, 380, 341, 342

(56) References Cited

U.S. PATENT DOCUMENTS

| | | |
|---|---|---|
| 5,250,548 | 10/1993 | Winn et al. ........................ 514/340 |
| 5,298,518 | 3/1994 | Mikake et al. .................... 514/381 |
| 5,328,919 | 7/1994 | Naka et al. ....................... 514/381 |
| 5,332,831 | 7/1994 | Dowle et al. ..................... 548/315 |
| 5,591,762 | 1/1997 | Hauel et al. ...................... 514/381 |
| 5,830,909 | * 11/1998 | Crandall ........................... 514/381 |

FOREIGN PATENT DOCUMENTS

| | | |
|---|---|---|
| 2036427 | 8/1991 | (CA) . |
| 2057913 | 10/1991 | (CA) . |
| 2050723 | 3/1992 | (CA) . |
| 0 253 310 | 1/1988 | (EP) . |
| 0 403 159 | 12/1990 | (EP) . |
| WO 93/20816 | 10/1993 | (WO) . |
| 95/24901 | * 9/1995 | (WO) .................................. 514/381 |
| WO 95/33454 | * 12/1995 | (WO) . |

OTHER PUBLICATIONS

Hamlet, P. et al. 1996, J. Hypertens, vol. 14, suppl. 1, S140 (abstract 9A.1).
Bunkenburg, B. et al. 1991, Hypertension, vol. 18(3), pp. 278–288.
Cigola, E. et al. 1997, Experimental Cell Research, vol. 231, pp. 363–371.
deBlois, D, et al. 1997, Hypertension, vol. 29, pp. 340–349.
deGasparo, M. et al. 1992, Cellular and Molecular Biology of the Adrenal Cortex, John Libbey Eurotext Ltd, vol. 222, pp. 3–17.
Hamlet P. et al. 1995, Curr Opin Nephrol Hypertens, vol. 4, pp. 1–7.
Hamlet, P. et al. 1995, Hypertension, vol. 26, pp. 641–648.
Herbert, J. et al. 1994, European Journal of Pharmacology vol. 251, pp. 143–150.
Horiuch, M. et al. 1997, The Journal of Biological Chemistry, vol. 272(30), pp. 19022–19026.
Horiuchi, T. et al. 1996, J. Hypertens, vol. 14, suppl. 1 S140 (abstract 9A.2).
Kajstura, J. et al. 1997, J. Mol. Cell Cardiol, vol. 29, pp. 859–870.
Kawamura, M. et al. 1993, The Journal of Pharmacology and Experimental Therapeutics, vol. 266(30), pp. 1654.
Koh, E. et al. 1994, Journal of Cardiovascular Pharmacology, vol. 23, pp. 175–179.
Pierzchalski, P. et al. 1997, Experimental Cell Research, vol. 234, pp. 57–65.
Taguchi, J. et al. 1994, Blood Pressure, vol. 3, (Suppl. 5), pp. 38–42.
Yamada, T. et al. 1996, Proc. Natl. Acad. Sci., vol. 93, pp. 156–160.
Zorad, S. et al. 1995, Gen. Physiol. vol. 14, pp. 383–391.

* cited by examiner

*Primary Examiner*—Frederick Krass
(74) *Attorney, Agent, or Firm*—Gregory D. Ferraro

(57) ABSTRACT

The invention provides the use of an AT$_1$ receptor antagonist, or a pharmaceutical salt thereof, for producing a pharmaceutical preparation for the stimulation of apoptosis and for the treatment of pathological symptoms which are substantially reduced, halted or prevented by apoptosis, and also corresponding pharmaceutical preparations.

4 Claims, No Drawings

AT₁ RECEPTOR ANTAGONIST FOR THE STIMULATION OF APOPTOSIS

This is a 371 of international application PCT/EP 97/00757 filed Feb. 18, 1997.

The enzyme cascade of the renin-angiotensin system (RAS) comprises a series of biochemical events and, as is well known, there are a variety of approaches for using regulatory intervention to open up treatment possibilities, for example treatment of hypertension.

Angiotensinogen, an α2-macroglycoprotein, is cleaved by the enzyme renin into the decapeptide angiotensin I, which is itself only very slightly active biologically. In the next step of the cascade, two further amino acids are cleaved off by the action of the enzyme angiotensin converting enzyme (ACE), which is mainly bound in the endothelium, with the formation of angiotensin II. The latter is regarded as being one of the most powerful natural vasoconstrictors.

The vasoconstrictive effects of angiotensin II are brought about by its action on the smooth muscle cells, and by stimulating formation of the adrenergic hormones adrenaline and noradrenaline and by increasing the activity of the sympathetic nervous system due to the formation of noradrenaline. In addition angiotensin II affects the electrolyte balance, generating, for example, antinatriuretic and antiuretic effects in the kidney, and consequently promotes release of the peptide vasopressin from the pituitary, on the one hand, and of aldosterone from the adrenal glomerulosa, on the other. All these effects play an important role in blood pressure regulation.

Angiotensin II interacts with specific receptors on the surface of the target cell. Success has by now been achieved in identifying receptor subtypes which are, for example, designated AT₁ receptors and AT₂ receptors. Recently, considerable efforts have been made to identify the substances which bind to the AT₁ receptor, with active compounds of this nature frequently being termed angiotensin II antagonists. As a consequence of the inhibition of the AT₁ receptor, these antagonists can, for example, be employed as antihypertensives or for treating congestive heart failure.

Angiotensin II antagonists are understood to mean those active compounds which bind to the AT₁ receptor subtype. This category includes compounds having differing structural features. For example, mention may be made of the compounds which are listed in the European Patent Application having the publication No. 443983 (EP 443983), in particular in the substance claims, the subject-matter of which claims is hereby incorporated into the present application by reference to this publication.

Preference is given to (S)-N-(1-carboxy-2-methylprop-1-yl)-N-pentanoyl-N-[2'(1H-tetrazol-5-yl)biphenyl-4-ylmethyl]amine [Valsartan] of the formula:

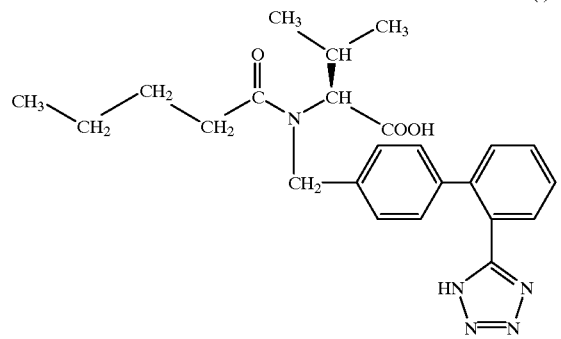

and its pharmaceutically utilizable salts.

Furthermore, the compounds which are listed in European Patent Application having the publication No. 253310 (EP 253310), in particular in the substance claims, are hereby incorporated into the present application by reference to this publication.

Preference is given to the compound [Losartan] of the following formula:

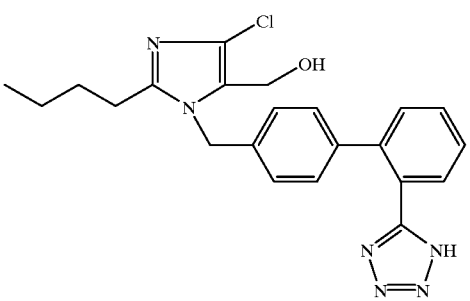

and its pharmaceutically utilizable salts.

Furthermore, the compounds listed in the European Patent Application having the publication No. 403159 (EP 403159), in particular in the substance claims, are hereby incorporated into the present application by reference to this publication.

Preference is given to the compound [Eprosartan] of the following formula:

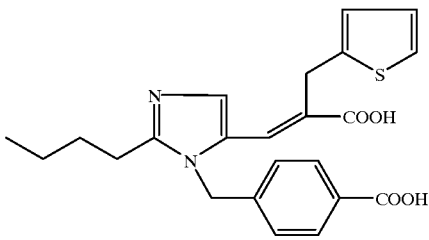

and its pharmaceutically utilizable salts.

Furthermore, the compounds listed in the PCT Patent Application having the publication No. WO 91/14679, in particular in the substance claims, are hereby incorporated into the present application by reference to this publication.

Preference is given to the compound [Irbesartan] of the following formula:

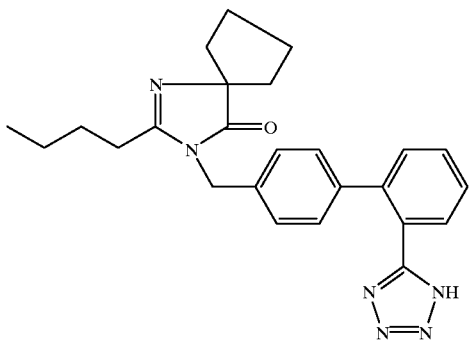

and its pharmaceutically utilizable salts.

Furthermore, the compounds listed in the European Patent Application having the publication No. EP 420237 (EP 420237), in particular in the substance claims, are hereby incorporated into the present application by reference to this publication.

Preference is given to the compound [E-1477] of the following formula:

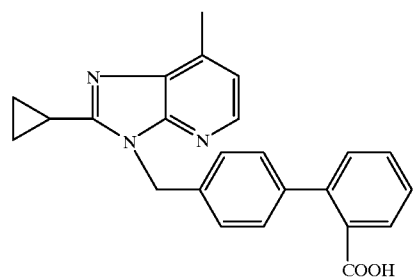

and its pharmaceutically utilizable salts.

Furthermore, the compounds listed in the European Patent Application having the publication No. 502314 (EP 502314), in particular in the substance claims, are hereby incorporated into the present application by reference to this publication.

Preference is given to the compound [Telmisartan] of the following formula:

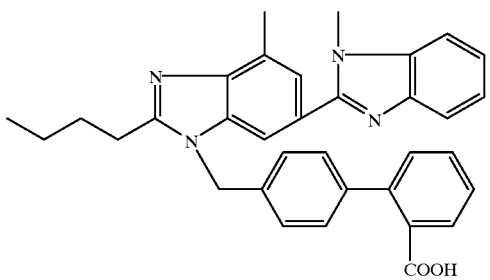

and its pharmaceutically utilizable salts.

Furthermore, the compounds listed in the European Patent Application having the publication No. 459136 (EP 459136), in particular in the substance claims, are hereby incorporated into the present application by reference to this publication.

Preference is given to the compound [Candesartan] of the following formula:

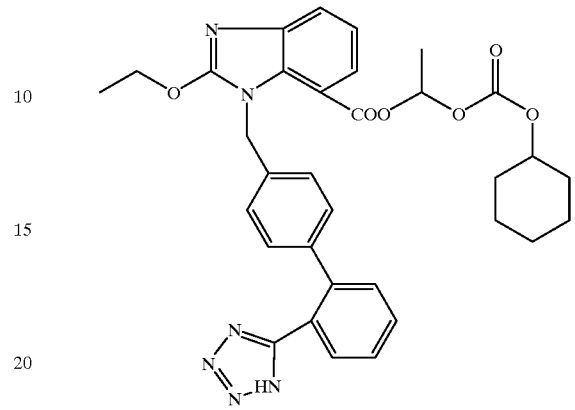

and its pharmaceutically utilizable salts.

Furthermore, the compounds listed in European Patent Application having the publication No. 504888 (EP 504888), in particular in the substance claims, are hereby incorporated into the present application by reference to this publication.

Preference is given to the compound [SC-52458] of the following formula:

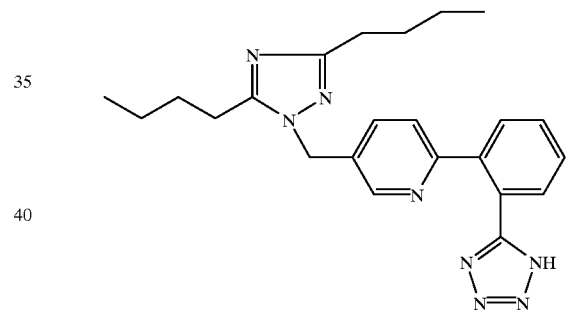

and its pharmaceutically utilizable salts.

Furthermore, the compounds listed in the European Patent Application having the publication No. 514198 (EP 514198), in particular in the substance claims, are hereby incorporated into the present application by reference to this publication.

Preference is given to the compound [Saprisartan] of the following formula:

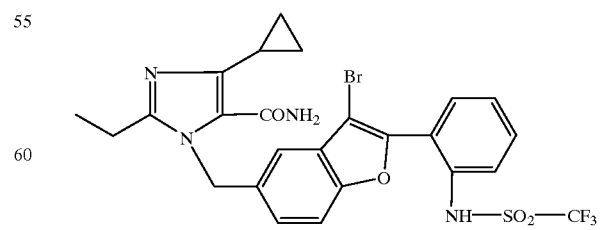

and its pharmaceutically utilizable salts.

Furthermore, the compounds listed in the European Patent Application having the publication No. 475206 (EP 475206), in particular in the substance claims, are hereby incorporated into the present application by reference to this publication.

Preference is given to the compound of the following formula:

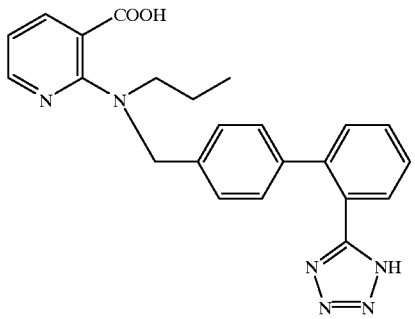

and its pharmaceutically utilizable salts.

Furthermore, the compounds listed in the PCT Patent Application having the publication No. WO 93/20816, in particular in the substance claims, are hereby incorporated into the present application by reference to this publication.

Preference is given to the compound [ZD-8731] of the following formula:

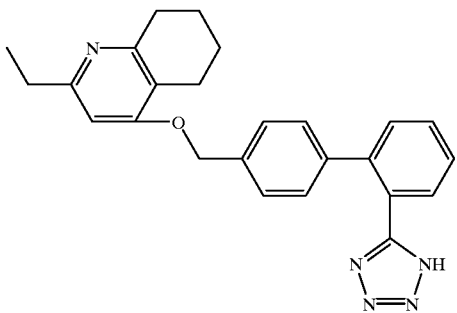

and its pharmaceutically utilizable salts.

$AT_1$ receptor antagonists which, for example, possess at least one basic centre can form acid addition salts. These are formed, for example, using strong inorganic acids, such as mineral acids, e.g. sulfuric acid, a phosphoric acid or a hydrohalic acid, using strong organic carboxylic acids, such as $C_1$–$C_4$alkanecarboxylic acids which are unsubstituted or substituted, for example, by halogen, e.g. acetic acid, such as saturated or unsaturated dicarboxylic acids, e.g. oxalic, malonic, succinic, maleic, fumaric, phthalic or terephthalic acid, such as hydroxycarboxylic acids, e.g. ascorbic, glycolic, lactic, malic, tartaric or citric acid, such as amino acids, e.g. aspartic or glutamic acid, or such as benzoic acid, or using organic sulfonic acids, such as $C_1$–$C_4$alkanesulfonic acids or arylsulfonic acids which are unsubstituted or substituted, for example, by halogen, e.g. methanesulfonic acid or p-toluenesulfonic acid. Examples of suitable salts with bases are metal salts, such as alkali metal or alkaline earth metal salts, e.g. sodium, potassium or magnesium salts, or salts with ammonia or an organic amine, such as morpholine, thiomorpholine, piperidine, pyrrolidine, a mono-, di- or tri-lower alkyl amine, e.g. ethyl-, tert-butyl-, diethyl-, diisopropyl-, triethyl-, tributyl- or dimethylpropyl-amines, or a mono-, di- or tri-hydroxy lower alkyl amine, e.g. mono-, di- or tri-ethanolamine. Furthermore, corresponding internal salts can be formed.

It has now been found, surprisingly, that $AT_1$ receptor antagonists stimulate the process of apoptosis.

Apoptosis plays an important role in morphogenesis, in dealing with hormonal and immunological responses and in the homeostatic balance of hypertrophy and atrophy. For example, apoptosis is the physiological mechanism which is involved in ovarian follicular atresia. Consequently, apoptosis is a fundamental physiological homeostatic process in multicellular organisms, playing an important role in the formation, shaping and maintenance of tissues. For example, damaged, precancerous and cancerous cells are eliminated in this process. Apoptosis requires active genetic transcription and translation and is correspondingly subject to genetic or epigenetic control. In this process, various morphological stages are passed through, which stages can generally be used as a base for establishing functional characterization. For example, apoptosis is induced by a signal, separation of adjacent cells takes place and the cytoplasm contracts. Condensation of the chromatin then takes place, followed by a fragmentation into membrane-bound apoptotic bodies. These latter are phagozytosed by neighbouring cells and broken down by the visiting cells using lysosomes. As previously mentioned, this course of events can be followed morphologically by means of monitoring with light microscopy or electron microscopy and also by means of molecular techniques, such as DNA laddering.

In the specialist literature, the term "programmed cell death" is also used synonymously with apoptosis. However, in connection with the present invention, the apoptosis which is evoked by active substances will also be included in addition to the apoptosis which strictly speaking is genetically controlled.

Stimulation of apoptosis by $AT_1$ receptor antagonists can, for example, be established experimentally as follows:

Eight week-old spontaneously hypertensive rats (SHR) are treated over a period of eight weeks by the daily administration of 10 mg of an $AT_1$ receptor antagonist, for example Valsartan, per kg. For fixing, the dissected-out femoral artery is rinsed for 10 minutes at a flow rate of 5 ml/min. A solution of 2.5% glutaraldehyde in an 0.1 mole phosphate buffer at pH 7.4 is used as fixative. The temperature of the rinsing solution is 25° C. Following fixation, samples of the artery, each about 2–4 cm in length, are removed. These samples are post-fixed in $OsO_4$ (1%; 1 hour), dehydrated with alcohols and embedded in epon/araldite. Semi-thin sections of the vessels are cut in the transverse plane, stained for contrast with methylene blue/azure II and checked under a light microscope. The corresponding procedure is carried out using non-hypertensive rats (WKY) and hypertensive control animals (spontaneously hypertensive rats—SHR). In three out of 4 animals in each group, sections of the three different regions of the femoral arteries are prepared for light microscopy and/or electron microscopy. These sections are also stained with methylene blue/azure II for contrasting for light microscopy or stained for electron microscopy by treating them with uranyl acetate/lead citrate. The samples are examined in a negative control experiment.

Evaluation of the experiments following administration of Valsartan as compared with each respective control group gives the following result:

| Experiment | Animals | Block sections | LM | EM |
|---|---|---|---|---|
| (i) WKY control | 3 | 9 | 15 | 46 |
| (ii) SHR control | 4 | 9 | 9 | 60 |
| (iii) SHR + Valsartan | 4 | 9 | 16 | 58 |

[LM = light microscopy; EM = electron microscopy]

The results of the evaluation show the following:

Control tissue (WKY):

The appearance of the endothelium in this tissue is as expected in the case of cells which are tightly bound to the elastic lamina (EL). The EL appears flat with few gaps. In most cases, the smooth muscle cells (SMC) are in a state of disorder, with the cells themselves having a relatively unwrinkled periphery. They do not have the same regular organization as in the case of the Wistar rat, for example, and the WYK rat is therefore to be regarded as differing structurally.

The gap junctions are close together and no irregular changes are apparent.

SHR Rats:

The blood vessel wall is generally thicker and the endothelium is no longer one single layer of cells, but it is instead replaced by a mixture of cells and collagen which is present between the endothelium and the EL. There are many tears or thinner regions in the lamina.

The gap junctions in the endothelium display extensive invaginations and long tongues on the luminal side.

Valsartan:

Treatment with Valsartan results in a different appearance as compared with that of the controls. It is possible to observe a certain degree of vacuole formation in the endothelial layer, zones containing collagen, extended tracts of still apparent SMC and the occasional appearance of markedly dense cells. In was possible to see these dense SMC cells, which possess large empty vacuoles and which are distributed over the whole of the vessel wall in an irregularly scattered manner, in the light microscope. The nuclei in these cells have a different appearance as compared with those of normal cells, with these dense SMC cells being shrunken and having a very pronounced content of chromatin. Many cells have vacuoles which are filled with amorphous proteinaceous material. This phenomenon corresponds to that which occurs in apoptosis or programmed cell death. While the wall thickness in the regions which appear normal seems to correspond to that of normal cells, the dense cells indicate that the regression of the hypertrophy is still not complete. In some regions, the tissue structure is found to be extremely abnormal, with cell processes which proceed from one cell through the cytoplasm into other cells.

While endothelial gap junctions are not visibly altered, it is possible to observe a slight increase in the separation of the endothelium from the underlying lamina.

The change in the cell wall thickness following treatment with an $AT_1$ receptor antagonist is very advantageous and must be assumed to be a general feature of the $AT_1$ receptor antagonist class of active compounds.

Frequency, in per cent, of cell types or cell structures:

|  | WKY | SHR | SHR + Valsartan |
|---|---|---|---|
| Very regular cell arrangement | 95% | 75% | 25% |
| necrotic/hypoxic | — | 7% | 5% |
| vacuolated cells | — | — | 10% |
| apoptotic cells | — | — | 45% |

The results from these investigations unambiguously demonstrate a surprisingly significant appearance of apoptotic cells when hypertensive animals are treated with the $AT_1$ receptor antagonist Valsartan. Accordingly, it is to be deduced from this that $AT_1$ receptor antagonists stimulate apoptosis.

Accordingly, $AT_1$ receptor antagonists can be used in therapeutically effective quantities to stimulate apoptosis and are consequently suitable for the treatment of pathological symptoms which are substantially reduced, halted or prevented by apoptosis.

$AT_1$ receptor antagonists and their pharmaceutically utilizable salts can, therefore, be used in therapeutically effective quantities for the treatment of vascular proliferation disturbances, including vascular cell wall hypertrophy which follows a thrombosis, angioplasty, Bürger's disease, atherosclerosis and arteriosclerosis.

Apoptosis occurs, for example, in malignant tumours, with the growth of these tumours frequently being retarded. In particular, apoptotic effects are found in increased quantity in tumours which react to irradiation, cytotoxic chemotherapy and hormonal ablation.

In general, substances which stimulate apoptosis can be employed in those cases where there is abnormal cell growth, for example in order to initiate endometric and prostatic regression (endometriosis, prostate hypertrophy and reduce the size of fat storage cells (obesity).

Such areas of application lie, for example, in the field of cancer treatment (e.g. in order to suppress unimpeded cell proliferation), in the treatment of immunosuppressive disorders and also in the achievement of resistance to chemotherapies or radiotherapies. Blood vessels can also be regulated or restored, e.g. following restenosis, by stimulating apoptosis.

The invention provides pharmaceutical preparations, which comprise an $AT_1$ receptor antagonist or a pharmaceutically utilizable salt thereof, for stimulating apoptosis and for treating pathological symptoms which are substantially reduced, halted or prevented by apoptosis.

The invention also provides the use of an $AT_1$ receptor antagonist, or a pharmaceutical salt thereof, for producing a pharmaceutical preparation for the stimulation of apoptosis and for the treatment of pathological symptoms which are substantially reduced, halted or prevented by apoptosis.

The invention furthermore provides a process for stimulating apoptosis and for treating pathological symptoms which are substantially reduced, halted or prevented by apoptosis, which comprises administering a therapeutically effective quantity of an $AT_1$ receptor antagonist or a pharmaceutical salt thereof.

The invention also provides the use of an $AT_1$ receptor antagonist, or a pharmaceutical salt thereof, for stimulating apoptosis and for treating pathological symptoms which are substantially reduced, halted or prevented by apoptosis.

These pharmaceutical preparations are for enteral, such as oral, and also rectal or parenteral, administration to homeotherms, with the preparations comprising the pharmacological active compound either alone or together with customary pharmaceutical auxiliary substances. For example, the pharmaceutical preparations consist of from about 0.1% to 100%, preferably of from about 1% to about 80%, of the active compound. Pharmaceutical preparations for enteral or parenteral, and also for ocular, administration are, for example, in unit dose forms, such as coated tablets, tablets, capsules or suppositories and also ampoules. These are prepared in a manner which is known per se, for example using conventional mixing, granulation, coating, solubulizing or lyophilizing processes. Thus, pharmaceutical preparations for oral use can be obtained by combining the active compound with solid excipients, if desired granulating a mixture which has been obtained, and, if required or necessary, processing the mixture or granulate into tablets or coated tablet cores after having added suitable auxiliary substances.

Suitable excipients are, in particular, fillers, such as sugars, for example lactose, sucrose, mannitol or sorbitol, cellulose preparations and/or calcium phosphates, for example tricalcium phosphate or calcium hydrogen phosphate, and also binders, such as starch pastes, using, for example, maize starch, wheat starch, rice starch or potato starch, gelatin, gum tragacanth, methyl cellulose and/or polyvinylpyrrolidone, and, if desired, disintegrants, such as the abovementioned starches, and also carboxymethyl starch, crosslinked polyvinylpyrrolidone, agar or alginic acid or a salt thereof, such as sodium alginate. Adjuvants are first and foremost flow-regulating agents and lubricants, for example silicic acid, talc, stearic acid or salts thereof, such as magnesium, or calcium stearate, and/or polyethylene glycol. Coated tablet cores are provided with suitable coatings which may or may not be resistant to gastric juice, with use being made, inter alia, of concentrated sugar solutions, which, if desired, comprise arabic gum, talc, polyvinylpyrrolidone, polyethylene glycol and/or titanium dioxide, lacquer solutions in suitable organic solvents or solvent mixtures, or, for preparing coatings which are resistant to gastric juice, solutions of suitable cellulose preparations, such as acetyl cellulose phthalate or hydroxypropylmethyl cellulose phthalate. Dyes or pigments can be added to the tablets or coated tablet coatings, for example for the purpose of identifying or labelling different active compound doses.

Further pharmaceutical preparations which can be used orally are hard capsules made of gelatin and also soft, closed capsules made of gelatin and an emollient, such as glycerol or sorbitol. The hard capsules can comprise the active compound in the form of a granulate, for example admixed with fillers such as lactose, binders, such as starches, and/or glidants, such as talc or magnesium stearate, and, if desired, stabilizers. In soft capsules, the active compound is preferably dissolved or suspended in suitable liquids, such as fatty oils, paraffin oil or liquid polyethylene glycols, with it being possible to add stabilizers in this case as well.

Examples of suitable pharmaceutical preparations which can be used rectally are suppositories which consist of a combination of the active compound and a suppository groundmass. Examples of suitable suppository groundmasses are natural or synthetic triglycerides, paraffin hydrocarbons, polyethylene glycols and higher alkanols. In addition, gelatin rectal capsules can also be used which comprise a combination of the active compound and a groundmass substance. Examples of suitable groundmass substances are liquid triglycerides, polyethylene glycols and paraffin hydrocarbons. Aqueous solutions of an active compound in water-soluble form, for example of a water-soluble salt, and also suspensions of the active compound, such as appropriate oily injection suspensions, with suitable lipophilic solvents or vehicles, such as fatty oils, for example benne oil, or synthetic fatty acid esters, for example ethyl oleate or triglycerides, being used, or aqueous injection suspensions which combine viscosity-increasing substances, for example sodium carboxymethyl cellulose, sorbitol and/or dextran, and, if desired, stabilizers as well, are most suitable for parenteral administration.

The dosage of the active compound can depend on a variety of factors, such as mode of administration, homeothermic species, age and/or individual condition. Normally, in the case of oral administration, an approximate daily dose of from about 10 mg to about 250 mg, for example in the case of Valsartan of about 40 mg, 80 mg or 160 mg, is to be estimated for a patient of approximately 75 kg in weight.

The following example illustrates the above-described invention; however, it is not intended to restrict the scope of this invention in any manner.

FORMULATION EXAMPLE 1

A hard gelatin capsule which, for example, comprises (S)-N-(1-carboxy-2-methylprop-1-yl)-N-pentanoyl-N-[2' (1H-tetrazol-5-yl)biphenyl-4-ylmethyl]amine, as the active compound can, for example, be of the following composition:

Composition:

| | |
|---|---|
| (1) Active compound | 80.0 mg |
| (2) Microcrystalline cellulose | 110.0 mg |
| (3) Polyvidone K30 | 45.2 mg |
| (4) Sodium lauryl sulfate | 1.2 mg |
| (5) Crospovidone | 26.0 mg |
| (6) Magnesium stearate | 2.6 mg |

Components (1) and (2) are granulated together with a solution of components (3) and (4) in water. Components (5) and (6) are added to the dry granulate and the whole is used to fill size 1 hard gelatin capsules.

What is claimed is:

1. A method for treating pathological symptoms of vascular proliferation disorders which can be reduced or inhibited by apoptosis, which comprises administering to a subject in need thereof a therapeutically effective quantity of an $AT_1$ receptor antagonist or a pharmaceutical salt thereof, wherein the $AT_1$ receptor antagonist is selected from the group consisting of:

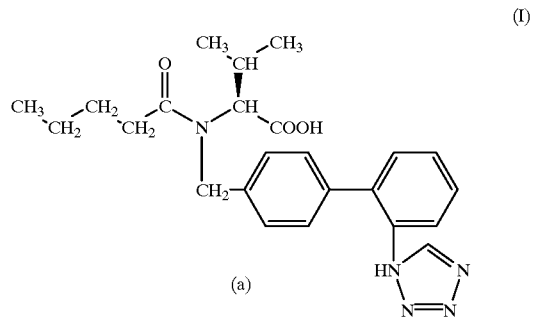

(a)

(I)

-continued

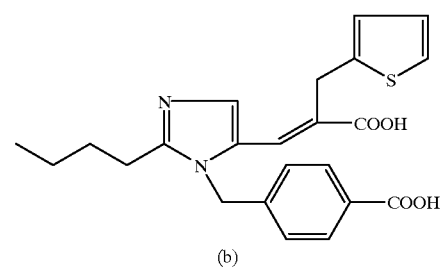
(b)

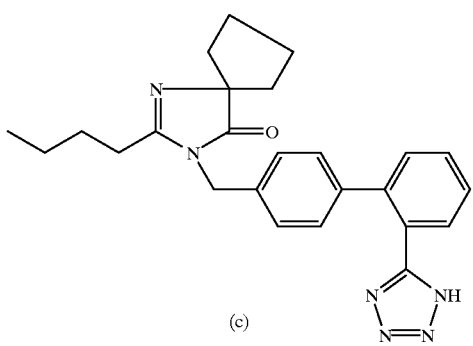
(c)

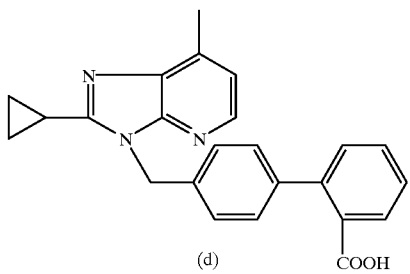
(d)

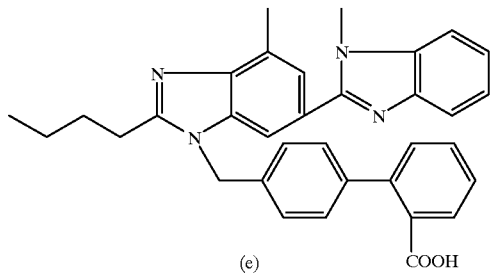
(e)

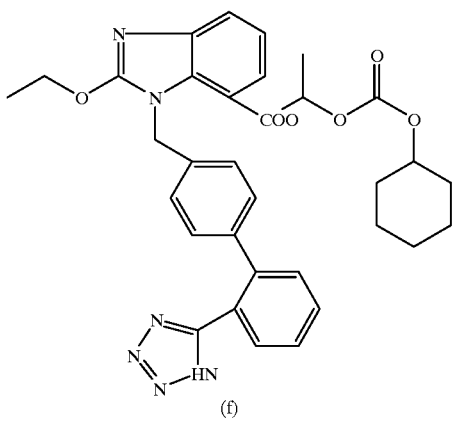
(f)

-continued

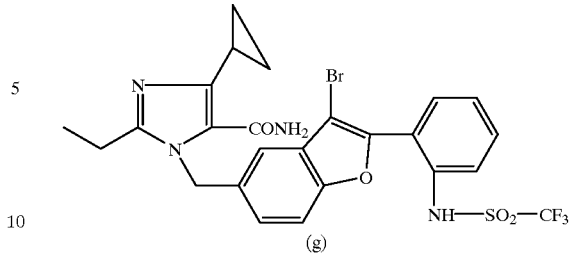
(g)

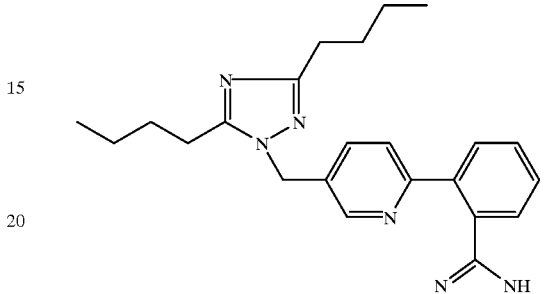
(h)
and

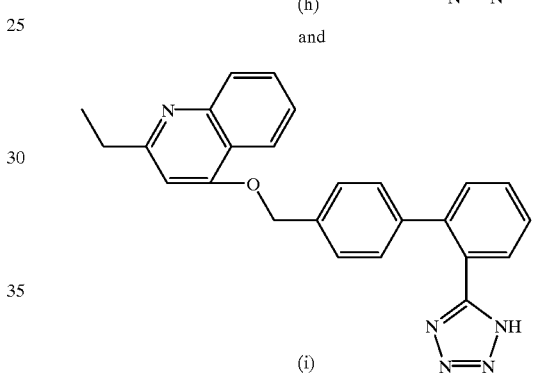
(i)

or in each case a pharmaceutically utilizable salt thereof, so as to stimulate apoptosis, thereby reducing or inhibiting said symptoms.

2. The method according to claim 1, wherein the treatment of pathological symptoms which can be reduced or inhibited by apoptosis comprises the suppression of cell proliferation.

3. The method according to claim 1, wherein the disorders are selected from the group consisting of restenosis and vascular cell wall hypertrophy following thrombosis, angioplasty, Burger's disease, atherosclerosis or arteriosclerosis.

4. A method for treating resistance to chemotherapy and/or radiotherapy which can be reduced or inhibited by apoptosis, comprising administering valsartan, eprosartan, irbesartan, E-1477, telmisartan, candesartan, saprisartan, SC-52458 or ZD-8731 to a subject in need thereof, so as to stimulate apoptosis, thereby reducing or inhibiting said resistance.

* * * * *